(12) United States Patent
Von Holst et al.

(10) Patent No.: US 8,287,940 B2
(45) Date of Patent: Oct. 16, 2012

(54) COATING METHOD FOR A FOLDED BALLOON

(75) Inventors: Armin Von Holst, Aachen (DE); Christoph Heitzmann, Berlin (DE)

(73) Assignee: B. Braun Melsungen AG, Melsungen (DE)

( * ) Notice: Subject to any disclaimer, the term of this patent is extended or adjusted under 35 U.S.C. 154(b) by 1001 days.

(21) Appl. No.: 12/279,019

(22) PCT Filed: Feb. 9, 2007

(86) PCT No.: PCT/DE2007/000242
§ 371 (c)(1),
(2), (4) Date: Nov. 4, 2008

(87) PCT Pub. No.: WO2007/090385
PCT Pub. Date: Aug. 16, 2007

(65) Prior Publication Data
US 2009/0054837 A1 Feb. 26, 2009

(30) Foreign Application Priority Data

Feb. 9, 2006 (DE) .......................... 10 2006 006 067

(51) Int. Cl.
*A61L 29/16* (2006.01)
(52) U.S. Cl. ...................... 427/2.28; 604/103.2; 427/2.1
(58) Field of Classification Search .......... 427/2.1–2.31; 103/103.02; *A61L 29/16*
See application file for complete search history.

(56) References Cited

U.S. PATENT DOCUMENTS

| | | | |
|---|---|---|---|
| 4,955,862 A | 9/1990 | Sepetka | |
| 5,049,131 A * | 9/1991 | Deuss | 604/98.01 |
| 5,102,402 A | 4/1992 | Dror et al. | |
| 5,370,614 A | 12/1994 | Amundson et al. | |
| 5,738,901 A | 4/1998 | Wang et al. | |
| 5,833,706 A | 11/1998 | St. Germain et al. | |
| 2003/0130717 A1 | 7/2003 | Hale et al. | |
| 2006/0020243 A1 * | 1/2006 | Speck et al. | 604/103.02 |
| 2006/0112536 A1 * | 6/2006 | Herweck et al. | 29/592 |
| 2007/0276461 A1 * | 11/2007 | Andreas et al. | 623/1.11 |
| 2009/0227949 A1 * | 9/2009 | Knapp et al. | 604/103.02 |
| 2010/0063585 A1 * | 3/2010 | Hoffmann et al. | 623/1.46 |
| 2010/0076542 A1 * | 3/2010 | Orlowski | 623/1.12 |
| 2010/0233228 A1 * | 9/2010 | Speck | 424/422 |
| 2010/0331816 A1 * | 12/2010 | Dadino et al. | 604/509 |
| 2011/0015664 A1 * | 1/2011 | Kangas et al. | 606/192 |
| 2011/0099789 A1 * | 5/2011 | Ewing et al. | 29/428 |

FOREIGN PATENT DOCUMENTS

| | | |
|---|---|---|
| DE | 90 07 751 U1 | 4/1995 |
| DE | 199 37 707 A1 | 3/2001 |
| EP | 0 692 276 A2 | 1/1996 |
| WO | WO 02 / 11808 A2 | 2/2002 |
| WO | WO-2004/028582 A1 | 4/2004 |

OTHER PUBLICATIONS

International Search Report and Written Opinion for Application No. PCT/DE2007/000242 dated Oct. 29, 2007.

* cited by examiner

*Primary Examiner* — David Buttner
*Assistant Examiner* — Brieann R Fink

(57) ABSTRACT

The present invention relates to compositions which are suitable for selective filling or selective coating of folds of a folded balloon, and especially relates to compositions of a contrast agent and an active agent in a solvent for filling of folds of a folded catheter balloon as well as to methods for selective filling or selective coating of folds of a folded catheter balloon and to filled or coated folded catheter balloons which can be obtained according to one of these methods.

10 Claims, 1 Drawing Sheet

COATING METHOD FOR A FOLDED BALLOON

The present invention relates to compositions which are suitable for selective filling or selective coating of folds of a folded balloon, and especially relates to compositions of a contrast agent and an active agent in a solvent for filling of folds of a folded catheter balloon as well as to methods for selective filling or selective coating of folds of a folded catheter balloon and to filled or coated folded catheter balloons which can be obtained according to one of these methods.

For the treatment of stenoses it is state of the art to implant stents or to dilatate the narrowed vascular region by so-called biological stenting. Therefore often stents and/or catheter balloons are used which are coated with a polymer as active agent carrier and an anti-restenotic active agent.

As usually the catheter balloon, with or without a mounted, i.e. crimped stent, has to pass a longer vessel route to arrive at the site of the vessel narrowing the problem of protecting the active agent against premature release from the stent and/or balloon arises.

With respect to stents different solutions for this problem have been proposed already. For example, US 2004/0071861 and WO 03/035131 A disclose that in the struts of the stent small cavities for receiving an active agent can be provided and that the active agent in the cavities can be protected by applying a protective coating.

WO 02/45744 A describes a stent without cavities which is provided with a first coating comprising an active agent and a superjacent inelastic covering layer which protects the active agent. The invention according to WO 02/45744 A shall be that upon expansion of the stent the inelastic covering layer breaks up and releases the active agent selectively at the site of its purpose.

For catheter balloons such covering layers are also thinkable, however, due to the large surface of the catheter balloon more difficulty to realize as practical embodiments.

The European Patent EP 0 519 063 B1 discloses the possibility of coating a folded catheter balloon with micro capsules, wherein in the micro capsules a pharmacological active agent can be included. Moreover, EP 0 519 063 B1 discloses the possibility of including a part of the micro capsules in the folds of the folded catheter balloon if the folded catheter balloon in the expanded, i.e. inflated state, is provided with micro capsules and then folded again, i.e. deflated (see claim 8 of EP 0 519 063 B1).

However, this embodiment has still the problem that only a part of the micro capsules is included in the folds and thus the amount of active agent which is present in the folds is unknown. The micro capsules which are not included in the folds are almost completely released from the balloon surface upon inserting the folded catheter balloon and do not arrive at the destination. Moreover, the method of coating according to EP 0 519 063 B1 is restricted to solids and especially to micro capsules and can not be used with liquids.

The object of the present invention was to apply the active agent in the active agent application via a catheter balloon in such a way that an undesired premature release does not occur.

The object is solved by providing an active agent-filled folded catheter balloon according to herein described embodiments as well as methods of coating as well as a composition which is suitable for these methods of coating. Further advantages designs, aspects and details of the invention are in the claims, description, examples and figures.

The object is solved by providing of methods of coating which coat the folded catheter balloon in the compressed or only minimally inflated state.

Thereby the amount of active agent within the folds is exactly known what is an important aspect for clinical approvals and additionally the active agents can be conveniently inserted in a dissolved form without a prior complicated provision of special pharmacological formulations such as micro capsules.

The methods of coating according to the invention are selectively coating the folds, i.e. are selectively filling the folds, wherein the remaining balloon surface which is not under the folds remains uncoated.

The selective filling of the folds is done via so-called punctual or linear coating methods. Not used are methods of dipping or spraying which cover the whole balloon surface. Moreover, the methods according to the invention are used with deflated and compressed or slightly inflated folded catheter balloons.

According to the invention a pipetting method is used which utilizes the capillary forces, a syringe method is used wherein a precision nozzle is moved relative to the longitudinal direction of the fold, or a spraying method is used wherein one or more precision nozzles being in series are inserted under the fold and which fill the fold at one or more points until the fold is completely filled.

Basically, in the methods according to the invention each fold is filled or coated separately. Before the next fold is filled or coated the content of the first fold can be dried, however, this is not necessary in each case. It is also possible to fill resp. to coat all of the folds sequentially and then to dry the content of all of the folds.

According to the invention drying is done under rotating the folded catheter balloon which is described in detail below.

Coating or filling of the folds is done with a liquid mixture comprising at least one active agent and a solvent or carrier. Moreover, also contrast agents, salts, adjuvants or other pharmacologically acceptable substances can be present.

As active agent any antiproliferative, antiinflammatory, antiphlogistic, cytostatic, cytotoxic, antiangiogenic, anti-restenotic or antithrombotic active agent can be used.

Examples of such active agents are abciximab, acemetacin, acetylvismione B, aclarubicin, ademetionine, adriamycin, aescin, afromoson, akagerine, aldesleukin, amidorone, aminoglutethemide, amsacrine, anakinra, anastrozole, anemonin, anopterine, antimycotics, antithrombotics, apocymarin, argatroban, aristolactam-AII, aristolochic acid, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, Boswellic acids and derivatives thereof, bruceanoles A, B and C, bryophyllin A, busulfan, antithrombin, bivalirudin, cadherins, camptothecin, capecitabine, o-carbamoyl-phenoxy-acetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-type Natriuretic Peptide (CNP), cudraisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, daunomycin, epirubicin, epothilones A and B, erythromycin, estramustine, etoposide, everolimus, filgrastim, fluoroblastin, fluvastatin, fludarabine, fludarabine-5'-dihydrogenphosphate, fluorouracil, folimycin, fosfestrol, gemcitabine, ghalakinoside, ginkgol, ginkgolic acid, glycoside 1a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, irinotecan, topotecan, hydroxycarbamide, miltefosine, pentostatin, pegaspargase, exemestane, letrozole, formestane, SMC proliferation inhibitor-2ω, mitoxantrone, mycophenolate mofetil, c-myc antisense, b-myc antisense, β-lapachone, podophyllotoxin, podophyllic acid 2-ethylhydrazide, molgramostim (rhuGM-CSF), peginterferon α-2b, lanograstim (r-HuG-CSF), macrogol, selectin (cytokine antagonist), cytokinin inhibitors, COX-2 inhibitor, NFkB, angiopeptin, monoclonal antibodies which inhibit the muscle cell proliferation, bFGF antagonists, probucol, prostaglandins, 1-hydroxy-11-methoxycanthin-6-one, scopoletin, NO donors, pentaerythritol tetranitrate, sydnonimines, S-nitrosoderivatives, tamoxifen, staurosporine, β-estradiol, α-estradiol, estriol, estrone, ethinylestradiol, medroxyprogesterone, estradiol cypionates, estradiol benzoates, tranilast, kamebakaurin and other terpenoids which are applied in the therapy of cancer, verapamil, tyrosine kinase inhibitors (tyrphostins), paclitaxel, derivatives and analoga of paclitaxel, 6-α-hydroxy-paclitaxel, 2'-succinylpaclitaxel, 2'-succinylpaclitaxeltriethanolamine, 2'-glutarylpaclitaxel, 2'-glutarylpaclitaxeltriethanolamine, 2'-O-ester of paclitaxel with N-(dimethylaminoethyl)glutamide, 2'-O-ester of paclitaxel with N-(dimethylaminoethyl)glutamidhydrochloride, taxotere, macrocyclic oligomers of carbon suboxide (MCS), mofebutazone, lonazolac, lidocaine, ketoprofen, mefenamic acid, piroxicam, meloxicam, penicillamine, hydroxychloroquine, sodium aurothiomalate, oxaceprol, β-sitosterin, myrtecaine, polidocanol, nonivamide, levomenthol, ellipticine, D-24851 (Calbiochem), colcemid, cytochalasin A-E, indanocine, nocadazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics, cefadroxil, cefazolin, cefaclor, cefoxitin, tobramycin, gentamycin, penicillins, dicloxacillin, oxacillin, sulfonamides, metronidazole, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamine, prourokinase, streptokinase, warfarin, urokinase, vasodilators, dipyridamol, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, p65, NF-kB, Bcl-xL antisense oligonucleotides, halofuginone, nifedipine, tocopherol, tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecainide, propafenone, sotolol, natural and synthetically obtained steroids, inotodiol, maquiroside A, ghalakinoside, mansonine, strebloside, hydrocortisone, betamethasone, dexamethasone, non-steroidal substances (NSAIDS), fenoprofen, ibuprofen, indomethacin, naproxen, phenylbutazone, antiviral agents, ayclovir, ganciclovir, zidovudin, clotrimazole, flucytosine, griseofulvin, ketoconazole, miconazole, nystatin, terbinafine, antiprotozoal agents, chloroquine, mefloquine, quinine, natural terpenoids, hippocaesculin, barringtogenol-C21-angelat, 14-dehydroagrostistachin, agroskerin, agrostistachin, 17-hydroxyagrostistachin, ovatodiolids, 4,7-oxycycloanisomel acid, baccharinoids B1, B2, B3 and B7, tubeimoside, bruceantinoside C, yadanziosides N and P, isodeoxyelephantopin, tomenphantopin A and B, coronarin A, B, C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterin, protoanemonin, cheliburin chloride, sinococuline A and B, dihydronitidine, nitidine chloride, 12-beta-hydroxypregnadien-3,20-dion, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, maytansin, lycoridicin, margetine, pancratistatin, liriodenine, bisparthenolidine, oxoushinsunine, periplocoside A, ursolic acid, deoxypsorospermin, psycorubin, ricin A, sanguinarine, manwu wheat acid, methylsorbifolin, spatheliachromen, stizophyllin, mansonine, strebloside, dihydrousambaraensine, hydroxyusambarine, strychnopentamine, strychnophylline, usambarine, usambarensine, liriodenine, oxoushinsunine, daphnoretin, lariciresinol, methoxylariciresinol, syringaresinol, sirolimus, rapamycin, somatostatin, tacrolimus, roxithromycin, troleandomycin, simvastatin, rosuvastatin, vinblastine, vincristine, vindesine, teniposide, vinorelbine, trofosfamide, treosulfan, temozolomide, thiotepa, tretinoin, spiramycin, umbelliferone, desacetylvismione A, vismione A and B, zeorin as well as mixtures of said active agents.

Especially preferred active agents are rapamycin (sirolimus) and paclitaxel, derivatives and analogues of paclitaxel, 6-α-hydroxy-paclitaxel, 2'-succinylpaclitaxel, 2'-succinylpaclitaxeltriethanol-amine, 2'-glutarylpaclitaxel, 2'-glutarylpaclitaxeltriethanolamine, 2'-O-ester of paclitaxel with N-(dimethylaminoethyl)glutamide, 2'-O-ester of paclitaxel with N-(dimethylaminoethyl)glutamidehydrochloride, taxotere as well as mixtures of said active agents. Especially preferred is paclitaxel.

Of course, also active agent mixtures can be used, such as an active agent mixture of paclitaxel and trapidil or of paclitaxel with an NO-donor or of rapamycin with vitamin A or vitamin C.

Also important is the used solvent which is removed by drying at atmospheric pressure or under vacuum after filling the folds.

As solvents lightly volatile organic compounds such as dichloromethane, chloroform, ethanol, acetone, heptane, n-hexane, DMF, DMSO, methanol, propanol, tetrahydrofurane (THF), methylenechloride, ethers, petrolether, acetic acid ester, cyclohexane can be used. In the selection of the solvent it is particularly important that it does not attack resp. renders the material of the folded catheter balloon unusable resp. that the contacting time of the solvent is such short that no damaging occurs resp. that an eventual damaging is irrelevant and does not result in damages which could lead to bursting of the balloon during dilatation.

As solvents preferably alcohols and especially diols and triols also in combination with monools have proved of value. The preferred solvent can especially selected from the following group: methanol, ethanol, isopropanol, n-butanol, isobutanol, t-butanol, ethyleneglycol, propyleneglycol, 1,3-propanediol, butyleneglycol, 1,3-butanediol, 1,4-butanediol, glycerin, 1,2,3-butanetriol, 1,2,4-butanetriol and 1,2,3,4-butanetetraol, wherein also mixtures of these solvents as well as mixtures of the above mentioned organic solvents can be used. Preferred are ethyleneglycol, propyleneglycol, 1,3-propanediol, butyleneglycol, 1,3-butanediol, 1,4-butanediol and especially preferred is glycerin.

Also water can be contained in the solvent mixture, however, preferably in an amount lower than 50% by weight, preferred 30% by weight and especially preferred 10% by weight with respect to the total solution.

Depending on the method of coating according to the invention thin viscous solutions of the active agent of thick viscous solutions of the active agent or active agent combination are required.

Viscosity measurements are known by a skilled person and are preferably done with viscosimeters. The viscosity has to be adjusted according to the type and design of the folds.

Different types of folds and embodiments of folded catheter balloons are disclosed for example in EP 0 519 063 B1, WO 94/23787 A1 or WO 03/059430 A1. However, as almost every catheter balloon which can be deflated resp. dilated has folds the coating methods according to the invention can be used basically with every inflatable catheter balloon and are not restricted to the special embodiments mentioned in WO 94/23787 A1 or WO 03/059430 A1.

As solvents can be used besides of the above mentioned or together with the above mentioned solvents also oils, fatty acids and fatty acid esters. Preferred oils are for example: linseed oil, flax oil, hempseed oil, corn oil, walnut oil, rape oil, soy bean oil, sun flower oil, poppy-seed oil, safflower oil, wheat germ oil, safflower oil, grape-seed oil, evening primrose oil, borage oil, black cumin oil, algae oil, fish oil, cod-liver oil and/or mixtures of said oils.

Undiluted oils are used as solvents in the event when a thick viscous coating solution is required. By adding lipophilic solvents the viscosity can be lowered and thus a desired viscosity level can be adjusted. On the other hand thin viscous solutions can be increased in their viscosity by adding oils or fats.

The term "solution" or "coating solution" as used herein shall not only relate to clear solutions but also emulsions, dispersions and suspensions of one or more active agents in a solvent or solvent mixture optionally with other carriers, adjuvants or for example contrast agents.

The term "composition" or "active agent-containing composition" as used herein shall not only relate to solutions but also emulsions, dispersions, suspensions, oils, pastes, and viscous mixtures containing at least one pharmacological active agent. However, these compositions are not solid but liquid to viscous or in the form of a gel or paste.

As oils or basically as lipophilic substances natural and synthetic oils, fats, lipids, lipoids and waxes can be used.

WO 03/022265 A1 describes for example oily formulations of paclitaxel which can be used also and which are preferred. Comparable solutions of oils can be made also with other active agents such as trapidil or rapamycin.

Further examples for suitable oils or lipophilic substances can be represented by the following general formulae:

wherein

R, R', R", R* and R** are independently of each other alkyl, alkenyl, alkinyl, heteroalkyl, cycloalkyl, heterocyclyl groups having 1 to 20 carbon atoms, aryl, arylalkyl, alkylaryl, heteroaryl groups having 3 to 20 carbon atoms or functional groups and preferably represent the following groups: —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —NO$_2$, —F, —Cl, —Br, —I, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CON(CH$_3$)$_2$, —CON(C$_2$H$_5$)$_2$, —CON(C$_3$H$_7$)$_2$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO$_2$CH$_3$, —SO$_2$C$_2$H$_5$, —SO$_2$C$_3$H$_7$, —SO$_3$H, —SO$_3$CH$_3$, —SO$_3$C$_2$H$_5$, —SO$_3$C$_3$H$_7$, —OCF$_3$, —OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CO—N(CH$_3$)$_2$, —NH—CO—N(C$_2$H$_5$)$_2$, —O—CO—NH$_2$, —O—CON-HCH$_3$, —O—CONHC$_2$H$_5$, —O—CO—NHC$_3$H$_7$, —O—CO—N(CH$_3$)$_2$, —O—CO—N(C$_2$H$_5$)$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_3$, —C$_2$H$_5$, —C$_3$H$_7$, -cyclo-C$_3$H$_5$, —CH(CH$_3$)$_2$, —C(CH$_3$)$_3$, —C$_4$H$_9$, —CH$_2$—CH(CH$_3$)$_2$, —CH(CH$_3$)—C$_2$H$_5$, -Ph, —CH$_2$-Ph, —CPh$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH=C(CH$_3$)$_2$, —C≡CH, —C≡C—CH$_3$, —CH$_2$—C≡CH;

X is an ester group or amide group and especially —O-alkyl, —O—CO-alkyl, —O—CO—O-alkyl, —O—CO—NH-alkyl, —O—CO—N-dialkyl, —CO—NH-alkyl, —CO—N-dialkyl, —CO—O-alkyl, —CO—OH, —OH;

m, n, p, q, r, s and t are independently of each other integers from 0 to 20, preferred from 0 to 10.

The term "alkyl" for example in —CO—O-alkyl is preferably one of the alkyl groups mentioned for the aforesaid groups R, R' etc., such as —CH$_2$-Ph. The compounds of the aforesaid general formulae can be present also in the form of their salts as racemates or diastereomeric mixtures, as pure enantiomers or diastereomers as well as mixtures or oligo-

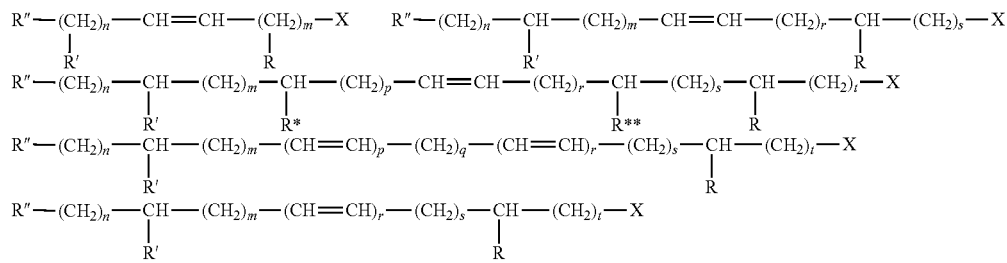

mers or copolymers or block copolymers. Moreover, the aforesaid substances can be used in mixture with other substances such as biostable and biodegradable polymers and especially in mixture with the herein mentioned oils and/or fatty acids. Preferred are such mixtures and individual substances which are suitable for polymerization, especially for auto polymerization.

Preferred are however naturally occurring oils, fatty acids and fatty acid esters, such as oleic acid, eicosapentaenoic acid, timnodonic acid, docosahexaenoic acid, arachidonic acid, linoleic acid, α-linolenic acid, γ-linolenic acid as well as mixtures and esters of said fatty acids. Especially preferred are omega-9 fatty acids, omega-3 fatty acids and omega-6 fatty acids as well as their esters and mixtures containing these substances preferably with a weight proportion of at least 10% by weight.

Further suitable fatty acids are listed in tables 1 to 4.

TABLE 1

Monoolefinic fatty acids

| Systematic name | Trivial name | Short form |
| --- | --- | --- |
| cis-9-tetradecenoic acid | myristoleic acid | 14:1(n-5) |
| cis-9-hexadecenoic acid | palmitoleic acid | 16:1(n-7) |
| cis-6-octadecenoic acid | petroselinic acid | 18:1(n-12) |
| cis-9-octadecenoic acid | oleic acid | 18:1(n-9) |
| cis-11-octadecenoic acid | vaccenic acid | 18:1(n-7) |
| cis-9-eicosenoic acid | gadoleinic acid | 20:1(n-11) |
| cis-11-eicosenoic acid | gondoinic acid | 20:1(n-9) |
| cis-13-docosenoic acid | erucinic acid | 22:1(n-9) |
| cis-15-tetracosenoic acid | nervonic acid | 24:1(n-9) |
| t9-octadecenoic acid | elaidinic acid | |
| t11-octadecenoic acid | t-vaccenic acid | |
| t3-hexadecenoic acid | | trans-16:1 (n-13) |

TABLE 2

Poly-unsaturated fatty acids

| Systematic name | Trivial name | Short form |
| --- | --- | --- |
| 9,12-octadecadienoic acid | linoleic acid | 18:2(n-6) |
| 6,9,12-octadecatrienoic acid | γ-linolenic acid | 18:3(n-6) |
| 8,11,14-eicosatrienoic acid | dihomo-γ-linolenic acid | 20:3(n-6) |
| 5,8,11,14-eicosatetraenoic acid | arachidonic acid | 20:4(n-6) |
| 7,10,13,16-docosatetraenoic acid | — | 22:4(n-6) |
| 4,7,10,13,16-docosapentaenoic acid | — | 22:5(n-6) |
| 9,12,15-octadecatrienoic acid | α-linolenic acid | 18:3(n-3) |
| 6,9,12,15-octadecatetraenoic acid | stearidonic acid | 18:4(n-3) |
| 8,11,14,17-eicosatetraenoic acid | — | 20:4(n-3) |
| 5,8,11,14,17-eicosapentaenoic acid | EPA | 20:5(n-3) |
| 7,10,13,16,19-docosapentaenoic acid | DPA | 22:5(n-3) |
| 4,7,10,13,16,19-docosahexaenoic acid | DHA | 22:6(n-3) |
| 5,8,11-eicosatrienoic acid | meadic acid | 20:3(n-9) |
| 9c,11t,13t-eleostearinoic acid | | |
| 8t,10t,12c-calendinoic acid | | |
| 9c,11t,13c-catalpicoic acid | | |
| 4,7,9,11,13,16,19-docosaheptadecanoic acid | stellaheptaenic acid | |
| | taxolic acid | all-cis-5,9-18:2 |
| | pinolenic acid | all-cis-5,9,12-18:3 |
| | sciadonic acid | all-cis-5,11,14-20:3 |

TABLE 3

Acetylenic fatty acids

| Systematic name | Trivial name |
| --- | --- |
| 6-octadecynoic acid | taririnic acid |
| t11-octadecen-9-ynoic acid | santalbinic or ximeninic acid |
| 9-octadecynoic acid | stearolinic acid |
| 6-octadecen-9-ynoic acid | 6,9-octadeceninic acid |
| t10-heptadecen-8-ynoic acid | pyrulinic acid |
| 9-octadecen-12-ynoic acid | crepenynic acid |
| t7,t11-octadecadiene-9-ynoic acid | heisterinic acid |
| t8,t10-octadecadiene-12-ynoic acid | — |
| 5,8,11,14-eicosatetraynoic acid | ETYA |

TABLE 4

Saturated fatty acids

| Systematic name | Trivial name | Short form |
| --- | --- | --- |
| dodecanoic acid | laurinic acid | 12:0 |
| tetradecanoic acid | myristinic acid | 14:0 |
| hexadecanoic acid | palmitinic acid | 16:0 |
| heptadecanoic acid | margarinic acid | 17:0 |
| octadecanoic acid | stearinic acid | 18:0 |
| eicosanoic acid | arachinic acid | 20:0 |
| docosanoic acid | behenic acid | 22:0 |
| tetracosanoic acid | lignocerinic acid | 24:0 |

Moreover, the esters of the fatty acids listed in tables 1-4 and especially their ethyl esters and mixtures containing these fatty acids and/or fatty acid esters are preferred. Further preferred fatty acids are 6,8-dithianoctanoic acid, γ-linolenic acid and α-liponic acid as well as their esters.

Moreover, also contrast agents can be included as additional substances in the composition which is to be inserted.

As matrix for receiving the active agent in the folds of the catheter balloon low molecular substances and especially contrast agents, contrast agent analogues or contrast agent-like substances have proved as suitable. As contrast agent analogues or contrast agent-like substances those substances are understood which are not entitled with the term "contrast agent" but have the characteristics of a contrast agent, namely to be visualized by imaging methods and diagnosis methods. With these substances mostly substances are concerned which contain barium, iodine, manganese, iron, lanthanum, cerium, praseodymium, neodymium, samarium, europium, gadolinium, terbium, dysprosium, holmium, erbium, thulium, ytterbium and/or lutetium.

As contrast agents common contrast agents for x-ray imaging, computer tomography (CT), magnetic resonance imaging or magnetic resonance tomography (MRT) can be used.

In principle, contrast agents are to be distinguished which are used in x-ray examinations (x-ray contrast agents) and those which are used in magnetic resonance tomography examinations (MR contrast agents), wherein the x-ray contrast agents such as Jod-Lipiodol® are preferred.

In the case of x-ray contrast agents substances are concerned which result in an increased absorption of penetrating x-rays with respect to the surrounding structure (so-called positive contrast agents) or which let pass penetrating x-rays unhindered (so-called negative contrast agents).

Moreover, iodine-containing contrast agents are preferred which are used in imaging of vessels (angiography and phlebography) and in CT (computer tomography).

Especially preferred are contrast agents having a 1,3,5-triiodobenzene nucleus, nephrotropic x-ray contrast agents having low osmolarity, amidotrizoic acid, iothalaminic acid, iotrolan, iopamidol, iodoxaminic acid, diatrizoic acid, iomeprol, iopromid, desmethoxyacetyl-iopromid (DAMI) or 5-amino-2,4,6-triiodophthalic acid-(2,3-dihydroxypropyl)-amide (ATH).

In the following some structures of the especially preferred contrast agents are shown:

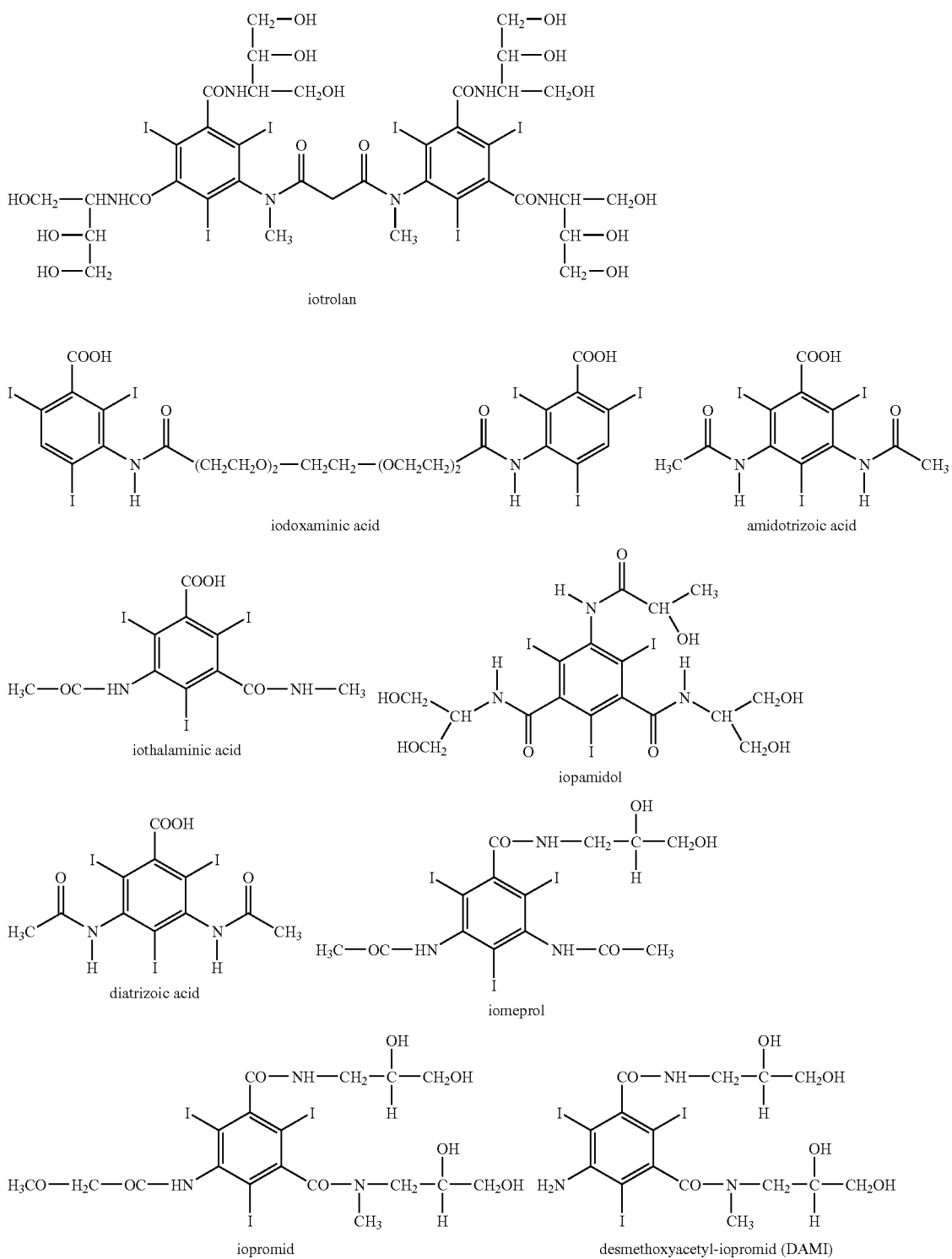

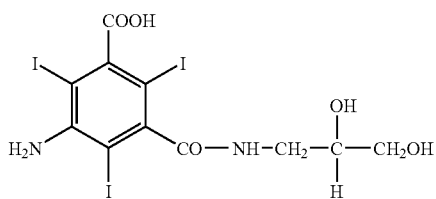

5-amino-2,4,6-triiodophthalic
acid-(2,3-dihydroxypropyl)-amide (ATH)

Another class of preferred contrast agents is represented by the paramagnetic contrast agents which contain mostly a lanthanide.

One of the paramagnetic substances which have unpaired electrons is e.g. gadolinium ($Gd^{3+}$) which has in total seven unpaired electrons. Further in this group are europium ($Eu^{2+}$, $Eu^{3+}$), dysprosium ($Dy^{3+}$) and holmium ($Ho^{3+}$). These lanthanides can be used also in chelated form by using for example hemoglobin, chlorophyll, polyaza acids, polycarboxylic acids and especially EDTA, DTPA as well as DOTA as chelator. Examples of gadolinium-containing contrast agents are gadolinium diethylenetriaminepentaacetic acid, gadopentetic acid (GaDPTA), gadodiamide, meglumin-gadoterate or gadoteridol.

According to the invention of course mixtures of two or more contrast agents can be used.

Moreover, physiologically acceptable salts can be present in the composition of the active agent or active agent mixture. Preferred are solutions or dispersions of an active agent, preferably paclitaxel or rapamycin and especially paclitaxel, together with one or more physiologically acceptable salts.

As salts preferably compounds can be used which contain sodium cations, calcium, magnesium, zinc, iron or lithium cations together with sulphate, chloride, bromide, iodide, phosphate, nitrate, citrate or acetate anions. As salts also ionic contrast agents can be used or ionic contrast agents can be added to the above mentioned salts.

To such a solution, dispersion or slurry the active agent or the active agent combination is added. As solvent preferably water is used, eventually with co-solvents. The salt content should be relatively high. In such salt solutions the main solvent is the water which can contain from up to 30% by weight, preferred 20% by weight and especially preferred up to a maximum of 10% by weight also one or more co-solvents.

Such salt solutions are mostly used for the syringe method.

This salt solution with active agent is syringed under the folds of the folded catheter balloon and is dried. The salt coating is very hygroscopic and thus has a high affinity to vessel tissue. During dilatation the folds open themselves and press the salty coating against the vessel wall. The salt coating then adheres to the vessel wall where it serves several purposes. On the one hand the local very high salt concentration results in a high isotonic pressure which bursts cells and on the other hand the high salt concentration dissolves also hard plaque and other depositions in the vessel and moreover releases the active agent which especially prevents the proliferation of smooth muscle cells.

After a few minutes up to a maximum of a couple of hours, depending on the amount, the salt coating transferred onto the vessel wall is completely dissolved.

Instead of or in combination with the aforementioned salts also amino acids, oligopeptides, polyamino acids, peptides and/or vitamins can be used.

Suitable amino acids are: glycine, alanine, valine, leucine, isoleucine, serine, threonine, phenylalanine, tyrosine, tryptophane, lysine, arginine, histidine, aspartate, glutamate, aspartic acid, glutamine, cysteine, methionine, proline, 4-hydroxyproline, N,N,N-trimethyllysine, 3-methylhistidine, 5-hydroxylysine, O-phosphoserine, γ-carboxyglutamate, ε-N-acetyllysine, ω-N-methylarginine, citrulline, ornithine and derivatives of these amino acids.

Suitable vitamins comprise: vitamin A, vitamin C (ascorbic acid), vitamin D, vitamin H, vitamin K, vitamin E, vitamin B1, vitamin B2, vitamin B3, vitamin B5, vitamin B6, vitamin B12, thiamine, riboflavin, niacin, pyridoxine and folic acid.

Moreover, also liposomal formulations of the active agent or active agent mixture can be used for the coating resp. filling of folded catheter balloons.

The liposomal formulations are preferably manufactured in that in a first step the active agent (e.g. paclitaxel or rapamycin) resp. the active agent combination is dissolved in an aqueous medium or buffer medium and then contacted with solutions which contain membrane-forming substances. With this method high insertion rates from at least 30% up to 95% result.

Membrane-forming substances are charged amphiphilic compounds preferably alkylcarboxy acids, alkylsulphonic acids, alkylamines, alkylammonium salts, phosphoric acid esters with alcohols, natural as well as synthetic lipids, such as phosphatidylglycerol (PG), phosphatidylserine (PS), derivatives of phophatidylethanolamine (PE derivatives) as well as of cholesterol, phosphatidic acid, phosphatidylinositol, cardiolipin, sphingomyelin, ceramide in its natural, semisynthetic or synthetic forms, stearylamine and stearic acid, palmitoyl-D-glucuronid and/or charged sphingolipids, such as sulphatide.

As neutral membrane-forming substances known components can be used, such as phosphatidylcholine (PC), phophatidylethanolamine (PE), steroids, preferably cholesterol, complex lipids and/or neutral sphingolipids.

The extraction of the liposomes from the aqueous solution is also done according to known methods, such as by dialysis, ultra filtration, gel filtration, sedimentation or flotation. The liposomes have an average diameter from 10 to 400 nm.

Such liposomal formulations can be preferably inserted into the folds of a folded catheter balloon via syringe method or capillary method (pipetting method).

The method of coating folds or method of filling folds according to the invention are the pipetting method also referred to as capillary method, the syringe method and the spraying method also referred to as method of spraying folds such as to clarify the difference to the unselective spraying method for the whole catheter balloon.

Thus, the present invention relates to methods of coating or filling the folds of a folded catheter balloon in the following way:

a) an active agent-containing composition is delivered at the distal or proximal end of a fold of the folded catheter balloon and the fold is filled due to capillary forces; or b) a syringe which delivers a continuous flow of an active agent-containing composition is moved relative to the folded catheter balloon along the fold; or c) a plurality of delivery openings being in series are pushed under the fold of the folded balloon and an active agent-containing composition is delivered simultaneously from the plurality of delivery openings into the fold.

It is advantageous that this coating or filling method is preferably performed in the compressed or deflated state or at maximum 10% inflated state of the catheter balloon. Under the term "10% inflated state" it is to be understood that the catheter balloon was subjected to 10% of inflation, i.e. the expansion, of the maximum expansion which is planned in the dilatation. If the expansion which is planned in the dilatation is referred to as 100% and the deflated state is set to 0% then a 10% inflation results according to the following formula:

$$(\text{diameter of the catheter balloon in the deflated state}) + (\text{diameter of the catheter balloon in the inflated state} - \text{diameter of the catheter balloon in the deflated state})/10$$

Moreover, by the methods according to the invention more or all of the folds can be coated of filled simultaneously and the coating or filling can be done selectively. A selective filling of the folds or selective coating of the folds shall mean that only the folds are filled or coated and the surface of the folded catheter balloon outside the folds is not coated.

A preferably used composition of active agent, solvent and contrast agent has the consistency of a paste or of a viscous mass or a viscous dispersion or emulsion or a tenacious pulp.

This composition has the advantage that it does not polymerize and that it maintains its consistency during the coating operation. This paste or (high) viscous mass or viscous slurry is inserted under pressure into the folds via a syringe device, preferably a nozzle, such as shown in FIG. 1.

If necessary, the nozzle can dilate the balloon folds and selectively fill the cavities formed by the folds. Usually the folded catheter balloons have 4 or more folds which are filled individually.

It was proven as especially advantageous to rotate the folded catheter balloon in the direction of the openings of the folds after filling of one or more or of all of the folds. This rotation results in that the viscous paste is dispersed completely and homogeneously in the folds and that eventual inclusions of air are released. The rotational direction is shown in FIG. 2. After rotation of the folded catheter balloon another filling of already filled or empty folds can be done.

During and/or after the rotation the composition in the folds dries under atmospheric pressure or under reduced pressure. Drying or curing of the composition is done by removing of the at least one alcohol by evaporation. The dried composition has a porous consistency and is released very easily from the balloon surface during dilatation. The alcohol as solvent was removed up to the usual residues and the contrast agent forms a porous matrix for the active agent and is moreover capable of releasing the active agent rapidly and in high concentration after dilatation of the folded catheter balloon. Moreover, the method according to the invention has the advantage to operate in a very material conserving way as only the folds are coated or filled and thus no active agent is present on the outer balloon surface which is lost during insertion of the catheter.

In the following the three coating and filling methods according to the invention are described in more detail.

Pipetting Method or Capillary Method:

In this method a pipette or syringe or another device capable of punctual delivery of the active agent-containing composition is used.

Under the term "active agent-containing composition" as used herein the mixture of active agent and solvent and/or adjuvant and/or carrier is understood, i.e. a real solution, dispersion, suspension or emulsion of an active agent or an active agent mixture and at least one further component selected from the herein mentioned solvents, oils, fatty acids, fatty acid esters, amino acids, vitamins, contrast agents, salts and/or membrane-forming substances. The term "solution" shall further clarify that a liquid mixture is concerned which, however, can be also viscous (thick viscous or high viscous).

The pipette or syringe or another device capable of punctual delivery of the active agent-containing composition is filled with the composition and preferably set at the proximal or at the distal end of a fold. The delivered composition is drawn into the fold and along the fold due to capillary forces until the opposite end of the fold is reached.

The catheter balloon is in the compressed, i.e. deflated, state. An even partial or slight inflation of the catheter balloon is usually not necessary for opening the folds a little. However, the filling of the folds can be done with a slight inflation of the catheter balloon of maximum 10% of the desired diameter during dilatation. Moreover, the filling of the folds can be done with a slight expansion of the folds in that 100 kPa (1 bar) positive pressure, preferred 50 kPa (0.5 bar) positive pressure are applied for slightly expanding the folds.

In this method it is important that the active agent-containing composition is sufficiently liquid to generate the respective capillary forces.

As compositions especially solutions of an active agent or active agent mixture in an alcohol or alcohol mixture are preferred.

The capillary forces should be that strong that a fold having a length of 10 mm is completely filled within 5 to 80 seconds, preferred within 15 to 60 seconds and especially preferred within 25 to 45 seconds.

If the composition resp. solution is too viscous it can be advantageous to tilt the catheter balloon with the fold to be filled from the horizontal position upwards for a maximum of 45°, preferred maximum of 30° and thereby to utilize also the force of gravity. Usually the filling of a fold is done via capillary forces, however, in the horizontal position of the catheter balloon with the fold to be filled upwards. The syringe or pipette or another device capable of punctual delivery of the active agent-containing composition is preferably set at the fold at the proximal or at the distal end of the fold sharp in the direction of the fold devolution in an angle of 10° to 65°, preferred 20° to 55°, more preferred in an angle of 27° to 50° and especially preferred in an angle of 35° to 45° measured from the horizontal.

Basically there is of course the possibility to set the syringe or pipette or another device capable of punctual delivery of the active agent-containing composition in the middle of the folds or at any other point located between the distal and proximal ends such that the fold is filled due to capillary forces simultaneously in the direction of the proximal and the distal ends, however the setting points at the end of the fold have proved as preferred.

If the composition for filling the folds resp. the present fold has reached the opposite end then the substance flow usually stops by itself and the syringe or pipette or another device capable of punctual delivery of the active agent-containing composition can be removed.

For not leaving a bigger drop of active agent-containing composition at the setting point of the syringe or pipette or another device capable of punctual delivery of the active agent-containing composition it has proved as advantageous to already remove the syringe or pipette or another delivery device before the active agent-containing composition has completely reached the other end of the fold. Thereby also the residual active agent-containing composition remaining at the setting point of the syringe or pipette or another delivery device is drawn into the fold such that no coating composition or filling composition remains outside the fold.

Preferably the syringe or pipette or another delivery device is removed when about 90% of the fold is filled with active agent-containing composition. The optimum point of time for removing the syringe or pipette or another delivery device can be exactly determined by a few experiments and is also reproducible.

The term "another device capable of punctual delivery of the active agent-containing composition" refers to a device which is capable like a pipette to deliver a constant and continuous flow of active agent-containing composition such that under this term a pump, micro pump or another reservoir can be understood which ensures this constant and continuous delivery of active agent-containing composition.

After filling a fold the catheter balloon is rotated such that the next fold to be coated is upwards and preferably horizontally. The filling operation of the folds is now repeated.

Depending on the consistency of the active agent-containing composition it can be necessary to dry the previously filled fold before the balloon is rotated to fill the next fold. Drying is done preferably by evaporation of the solvent.

Moreover, it is also possible in this method to fill or to coat simultaneously two, more than two or all of the folds of a catheter balloon if the consistency of the active agent-containing composition enables that, i.e. that the consistency is not that liquid that the composition leaks from the folds which are not in horizontal position.

Especially the pipetting method is suitable for the simultaneous filling or several or all of the folds of a catheter balloon. There the catheter balloon can be positioned horizontal or preferred perpendicular and the delivery devices are set from above at the ends of the folds preferably in an angle of 10 to 70 degrees such that the active agent-containing composition can flow into the folds.

If all of the folds of the balloon are filled the final drying is done. Basically, it is of course not necessary that all of the folds of the catheter balloon are filled wherein, however, the filling of all of the folds is the common and preferred embodiment as during dilatation a maximum possible amount of active agent shall be transferred to the vessel wall in a minimal possible time.

With the folded catheter balloons according to the invention dilatation is done preferably within a maximum of 60 seconds and especially preferred within a maximum of 30 seconds.

After filling the last fold drying of the last folds is done, i.e. of the content of the last fold, preferably without vacuum under normal pressure by evaporation of the solvent.

After this pre-drying a final drying can be done which is done according to the invention with a rotating catheter balloon. If it is necessary or desired a vacuum can be applied during rotation. This special drying method is described in more detail after the coating methods according to the invention.

Spraying Method or Syringe Method:

In this method according to the invention a precision syringe or needle or nozzle is set at the proximal or distal end of a fold and this delivery device in the form of a syringe, needle or nozzle is moved along the longitudinal direction of the fold relative to the fold and per covered partial distance a specified amount of an active agent-containing composition is delivered.

There, it is not important if the catheter balloon is fixed and the delivery device moves along the fold of if the delivery device is fixed and the catheter balloon moves relative thereto or if even the catheter balloon and the delivery device move relative to each other. If catheter balloon and delivery device should move relative to each other then a movement on a straight in opposite direction is preferred.

From the delivery device, i.e. syringe, needle or nozzle or the like, preferably a medium or thick viscous active agent-containing composition is delivered preferably in the form of a paste or a gel or an oil to the inside of the fold. The viscosities of preferred solutions are between $10^1$ to $10^6$ mPa·s, preferred between $10^2$ to $10^5$ mPa·s and especially preferred between $10^3$ to $10^4$ mPa·s.

Thus, especially suitable as active agent-containing compositions are such compositions with the above mentioned oils, alcohols (especially diols and polyols), fatty acids, fatty acid esters, amino acids, polyamino acids, membrane-forming substances, liposomal formulations and/or salts.

In the coating operation the tip of the syringe, nozzle or needle reaches about in the middle of the inside of the fold, thus about into the middle of the fold. There a continuous flow of the active agent-containing composition is delivered such that delivery rate and delivery amount in relation to the relative movement rate of delivery device and catheter balloon are suitable for filling the fold resp. the inside of the fold with the active agent-containing composition of at least 50% by volume, preferred at least 70% by volume and especially preferred at least 85% by volume.

Filling of one fold is done in about from 5 to 80 seconds, preferred about 15 to 60 seconds and especially preferred about 25 to 45 seconds in the case of a fold length of 10 mm.

The catheter balloon is in the compressed, i.e. deflated, state during the filling operation of the folds. An even partial or slight inflation of the catheter balloon is usually not necessary for opening the folds a little. However, the filling of the folds can be done with a slight inflation of the catheter balloon of maximum of 10% of the desired diameter during dilatation. Moreover, the filling of the folds can be done with a slight expansion of the folds in that 100 kPa (1 bar) positive pressure, preferred 50 kPa (0.5 bar) positive pressure are applied for slightly expanding the folds.

This coating method can be done of course with liquid active agent-containing compositions but is rather suitable for oily compositions as well as for high concentrated salt solutions.

Moreover, this method offers the advantage that more than one fold and especially all of the folds can be coated or filled simultaneously. There, an annular arrangement of delivery devices according to the number of folds is arranged such that per fold one delivery device is provided. With a small rotation the tips of the delivery devices are inserted into the folds and placed about centrally in the inside of the fold. With a relative and simultaneous movement of the delivery devices relative to the longitudinal direction of the folds all of the folds can be filled simultaneously with a continuous and constant flow of active agent-containing composition.

In coating or filling of one or all of the folds the catheter balloon can be in perpendicular or horizontal position or in a tilted position.

If in the active agent-containing composition volatile solvents were used then drying of the fold content can be necessary. With volatile solvents this is done preferably due to evaporation of the volatile solvent(s).

Then a final drying can be done, wherein the catheter balloon is rotated in the direction of the fold openings viewed from the inside of the folds. This method will be described in detail below.

Rotation of the catheter balloon in the direction of the fold openings can also serve to disperse the compositions which are in the folds or resp. under the folds equally in the respective fold.

This rotation of the folded catheter balloon can be advantageous especially in the use of oily or pasty active agent-containing compositions to ensure an equal dispersion of the active agent-containing composition in the folds as well as the inner surface of the folds.

As used herein the term "coating" relates therefore mainly to the coating of the inner surfaces of the folds, wherein the total inner space of the folds is usually not filled with active agent-containing composition resp. after drying with the remaining composition.

Contrary, the term "filling" relates to the complete filling of the inner space of the fold with active agent-containing composition.

If solvents are used which are removed by drying then usually a filling cannot be achieved and rather a coating of the inner surfaces of the folds exists.

If, however, substances having high boiling points, such as oil, are used as carriers or adjuvants then also a more or less complete filling of the folds is possible as long as no appreciable amounts of volatile substances are present in the active agent-containing composition.

This spraying method or syringe method is especially suitable for inserting active agent-containing compositions into the folds of folded catheter balloons which cannot be applied to a catheter balloon via common dipping or spraying methods not to mention to be inserted into the folds.

Contrary to the commonly used solid coatings on stents or catheter balloons the oily or pasty coatings and fillings offer the advantage that these active agent-containing compositions do not get dry totally but substantially maintain their consistency.

If at the location of the stenosed site the catheter balloon is inflated resp. dilated then this oily or pasty composition is transferred at least partially to the vessel wall and serves as active agent reservoir for a sustained active agent delivery of several hours to days for the surrounding tissue and has additionally the positive property to dissolve plaque and is then biologically degraded without releasing physiologically critical degradation products.

Spraying Method or Method of Spraying Folds:

In this method according to the invention a plurality of delivery openings being in series are pushed or inserted under the fold of the folded catheter balloon and simultaneously from the plurality of delivery openings an active agent-containing composition is delivered into the respective fold.

The delivery device consists preferably of 2 to 10 nozzles or delivery openings which are arranged in preferably equal distance along the longitudinal direction of the folds.

This delivery device is then inserted under the fold of the catheter balloon and the respective fold is filled or coated by simultaneous delivery of the active agent-containing composition form the nozzles or other delivery openings.

With this coating or filling variant it is not necessary that the delivery device is moved in the fold of the catheter balloon relative to the longitudinal direction of the fold. Usually catheter balloon and delivery device are fixed during the filling or coating, wherein a movement along the longitudinal direction of the fold is possible. If a relative movement is provided then the distance for the movement is preferably not bigger than the distance between two nozzles or delivery openings of the delivery device.

The delivery device comprises or consists of at least 2 and of a maximum of 10 delivery openings or nozzles or the like and preferred of 3 to 6 and especially preferred of 4 to 5 delivery openings or nozzles or the like which are arranged over a distance of 10 mm preferably equally.

The delivery device has 2 to 10 nozzles of similar openings which are capable of constantly delivering the active agent-containing composition or constantly spraying it into the fold.

For this filling or coating method preferably medium to thin viscous compositions or solutions of an active agent or active agent combination are used which contain especially an alcoholic solvent.

In this method of spraying folds the catheter balloon is in the compressed, i.e. deflated, state. An even partial or slight inflation of the catheter balloon is usually not necessary for opening the folds a little. However, the filling of the folds can be done with a slight inflation of the catheter balloon of maximum 10% of the desired diameter during dilatation. Moreover, the filling of the folds can be done with a slight expansion of the folds in that 100 kPa (1 bar) positive pressure, preferred 50 kPa (0.5 bar) positive pressure are applied for slightly expanding the folds.

After filling a fold the catheter balloon is rotated such that the next fold to be coated is preferably upwards and preferably horizontally. The filling operation of the folds or coating operation of the folds is now repeated.

Depending on the consistency of the active agent-containing composition it can be necessary to dry the previously filled fold before the balloon is rotated to fill the next fold. Drying is done preferably by evaporation of the solvent.

Moreover, it is also possible in this method to fill or to coat simultaneously two, more than two or all of the folds of a catheter balloon if the consistency of the active agent-containing composition enables that, i.e. that the consistency is not that liquid that the composition leaks from the folds which are not in horizontal position. For filling or coating of more or all of the folds a respective annular device of delivery devices is provided corresponding the number of folds, placed around the preferably perpendicularly arranged catheter balloon and the delivery openings are inserted by rotation under the folds, where the simultaneous delivery of the active agent-containing composition takes place.

If all of the folds of the balloon are filled the final drying is done. Basically, it is of course not necessary that all of the folds of the catheter balloon are filled wherein, however, the filling of all of the folds is the common and preferred embodiment as during dilatation a maximum possible amount of active agent shall be transferred to the vessel wall in a minimal possible time.

After filling the last fold drying of the last folds is done, i.e. of the content of the last fold, preferably without vacuum under normal pressure by evaporation of the solvent.

After this pre-drying a final drying can be done which is done according to the invention with a rotating catheter balloon. If it is necessary or desired a vacuum can be applied during rotation. This special drying method is described in more detail after the coating methods according to the invention.

Rotational Drying:

As mentioned above the coated or filled catheter balloons can be dried in the rotating state after filling or coating of every fold or after coating of filling of all of the folds or the folds to be coated resp. to be filled if not all of the folds shall be coated of filled.

This rotational drying has several advantages. First, thereby the active agent-containing composition is dried, and second, dispersed equally in the folds as well as on the surface within the folds.

The rotational drying is especially suitable with the oily or viscous active agent-containing compositions to achieve an equal dispersion of the composition in the respective fold.

Moreover, with the rotation of the catheter balloon vacuum can be applied to achieve an intense drying of the active agent-containing composition.

In drying in vacuum, especially with viscous, high viscous or solutions which pass into the solid state, superheating occurs, i.e. solvent residues which are occluded in the oil or solid are spontaneously released and tear or break the coating or filling. With drying in vacuum under simultaneous rotation this superheating is avoided and a dried continuous coating of the inner surface of the folds is obtained.

Moreover, the direction of rotation is decisive. The direction of rotation is done in the direction of the fold openings when viewed form the inner of the fold. In FIG. 2 the direction of rotation is shown and the catheter balloon is rotated as a paddle wheel of a paddle wheel excavator for pressing the active agent-containing composition due to the rotational force into the inside of the fold.

Preferably the folded catheter balloon is rotated with a rotational rate of 50 to 500, preferred 150 to 300 rotations per minute.

Depending on the active agent which is to be inserted into the folds or depending on the consistency of the active agent-containing composition which is to be inserted under the folds of a catheter balloon the suitable coating method according to the invention can be selected.

The fold spraying method is preferably suitable for thin viscous to medium viscous active agent-containing compositions while the pipetting method is preferably suitable for light viscous, medium viscous to light tough viscous compositions and the spraying method can be used especially well for medium viscous, viscous to high viscous compositions.

The term "viscosity" relates to the dynamic viscosity [η]:

$$[\eta] = \frac{kg}{m \cdot s} = Pa \cdot s = \frac{Ns}{m^2}$$

The spraying method can be used preferably with thick viscous compositions. Preferred are viscosities at room temperature in the range of oils (olive oil: $10^2$ mPa s), honey ($10^3$ mPa s), glycerine (1480 mPa s) or syrup ($10^5$ mPa s). Of course, this method works also with thin viscous solutions having $\eta \leq 10^2$ mPa s.

The pipetting method can be used preferably with medium viscous compositions. Preferred are viscosities at room temperature in the range of preferred 0.5 mPa s to 5000 mPa s, more preferred in the range of 0.7 mPa s to 1000 mPa s, more preferred in the range of 0.9 mPa s to 200 mPa s and especially preferred in the range of 1.0 mPa s to 100 mPa s. In this viscosity range are compositions of oils, contrast agents and/ or salts which are diluted with common solvents especially alcohols. The pipetting method can be used within a very broad viscosity range.

The fold spraying method can be used preferably with thin viscous compositions. Preferred are viscosities at room temperature in the range of preferred 0.1 mPa s to 400 mPa s, more preferred in the range of 0.2 mPa s to 100 mPa s and especially preferred in the range of 0.3 mPa s to 50 mPa s (water: 1.0 mPa s; petroleum: 0.65 mPa s; pentane: 0.22 mPa s; hexane: 0.32 mPa s; heptane: 0.41 mPa s; octane: 0.54 mPa s; nonane: 0.71 mPa s; chloroform: 0.56 mPa s; ethanol 1.2 mPa s; propanol 2.3 mPa s; isopropanol: 2.43 mPa s; isobutanol: 3.95 mPa s; isotridecanol: 42 mPa s).

Moreover, it was found surprisingly that a composition comprising at least a contrast agent and at least an antiproliferative, anti-inflammatory, antiphlogistic, cytostatic, cytotoxic, antiangiogenic, anti-restenotic or antithrombotic active agent and at least an alcohol as solvent is especially well suitable for the coating resp. filling of the folds of catheter balloons.

Intentionally, no polymer was used as active agent carrier which was difficultly to insert into the folds of the catheter balloon by the coating method according to the invention, which partially jammed the folds such that during dilatation of the folded catheter balloon an unequal opening of the folds and an unequal active agent delivery occurred.

In the syringe method for filling the folds of a folded catheter balloon preferably a precision nozzle or cannula is pushed under the fold and the mixture to be inserted is syringed into the fold, wherein preferably the nozzle or cannula is moved along the fold or with stationary nozzle or cannula the folded catheter balloon is moved in the longitudinal direction of the fold. This method enables a very precise and accurate coating of each fold resp. of the whole folded catheter balloon. An eventually used solvent evaporates or is removed under vacuum.

If the mixture or solution to be inserted has a consistency such that it can flow into the folds then the folded catheter balloon is positioned horizontal with one fold upwards or preferred tilted from 5 to 25 degrees such that the syringe or nozzle at the lower end of the folded catheter balloon can be set at the fold opening and that the mixture flows independently into the fold and fills it totally.

With these salt solutions having high salt content preferably water is used solvent as water does not react with the balloon material and does not damage it. As soon as the mixture has a consistency that it cannot leak from the fold anymore the folded catheter balloon is rotated and the next fold is filled until usually all of the 4 to 6 folds of the balloon are filled. Folded catheter balloons are preferred coated in the compressed state, wherein some special embodiments of folded catheter balloons can also be coated in the expanded state.

Such a coating method comprises the steps:
a) providing a folded catheter balloon
b) placing one fold of the balloon in a horizontal or up to 25 degrees tilted position,
c) setting the syringe opening at the fold opening facing the head end of the balloon,
d) executing a relative movement of syringe opening and folded catheter balloon in the longitudinal direction of the fold,
e) filling the fold during the movement operation with a mixture of an active agent and a salt and/or an ionic contrast agent in a suitable solvent, f) if necessary, drying the mixture which is present in the fold up to a degree which prevents leaking of the mixture from the fold,
g) rotating the balloon for 360° divided by the number of folds,
h) repeating steps b) to g) until all of the folds are filled, and
i) drying the mixtures in the folds until the mixture hardens.

If thin liquid mixtures are used then in step c) the syringe opening is set at the foot end and without relative movement according to step d) the fold is substantially filled due to capillary forces.

The present invention relates also to a method of opening narrowed vessel passages especially of cardiovascular vessels by short time dilatation. In this method during a maximum of 50 seconds, preferred a maximum of 40 seconds, more preferred a maximum of 30 seconds and especially preferred a maximum of 20 seconds a catheter balloon without stent is expanded and compressed again to a diameter of smaller than the 1.5 time starting diameter in the compressed state, wherein during this operation the vessel is only over expanded to a maximum of 10% of its diameter in the not narrowed state and per $mm^2$ balloon surface at least 20% of the active agent contained is delivered and mostly transferred to the vessel wall.

There, the transfer of the active agent preferably does not take place in pure form but in a matrix which at least within one hour after dilatation functions as active agent reservoir and delivers additional active agent to the vessel wall before it is dissolved or degraded.

Thus, this method is characterized in that in a possibly short time a possibly large amount of active agent is transferred locally and selectively to the vessel wall of a narrowed vessel site and that within the following 30 to 60 minutes a local active agent reservoir is ensured which is then dissolved or degraded.

For this method especially paclitaxel and paclitaxel derivatives as well as rapamycin proved as suitable.

Another method according to the invention relates to coating of catheter balloons with oily polymerizable substances. This method comprises the steps:
a) providing a catheter balloon (not folded catheter balloon),
b) providing a mixture which consists of at least 50% by weight of oily substances with at least one multiple bond and which contains at least an active agent,
c) applying a lubricant to the surface of the catheter balloon which substantially prevents the adhering of the oily substances on the surface of the catheter balloon,
d) applying the oily mixture on the lubricant resp. the lubricant layer on the catheter balloon,
e) rotating the catheter balloon during the coating step d),
f) initiating the polymerization via light, oxygen or radical initiators up to a not hard but elastic polymer layer,
g) eventually repeating the coating steps d) to f).

According to the herein disclosed methods catheter balloons can be selectively coated or filled within the folds such that the present invention relates to catheter balloons coated or filled in the folds which can be obtained according to the herein described methods.

The catheter balloons used are in the not dilated state in folds which form an accessible inner space that protects the substances contained therein. Possible forms of folded catheter balloons are described for example in WO 03/059430 A, WO 94/23787 A or EP 0 519 063 B1.

It is state of the art to use a folded catheter balloon and to insert a pharmacological active agent also into the folds of such a balloon. However, a method for a selective and exclusive and also complete filling of the folds is not known. The methods described in the cited documents are coating the balloon in the expanded state and insert a certain amount of the active agent with deflation in the folds, wherein the residual surface of the catheter balloon which is not in the folds is also coated.

The methods according to the invention selectively coat resp. fill the folds of the catheter balloon in the not expanded, i.e. folded, state. The catheter balloons coated or filled according to the invention are provided preferably for the cardiovascular field but can be used also for opening of all luminal structures, such as urinary passages, gullets, trachea, biliary tract, renal tract, small and large intestine, and especially of blood vessels within the whole body including brain, duodenum, and pylorus.

Thus, the coated or filled catheter balloons are especially suitable for preventing, reducing or treating stenoses, restenosis, arteriosclerosis, atherosclerosis and all other forms of a vessel occlusion or a vessel narrowing of passages or openings.

Moreover, the catheter balloons coated according to the invention are especially suitable for the treatment of in-stent restenosis, i.e. for the treatment of a renewed vessel narrowing within an already implanted stent which is preferably not bioresorbable. With suchlike in-stent restenosis the implantation of another stent within an already existing stent is especially problematic as usually the vessel can be dilated by the second stent to an only unsatisfying extent. Here, the application of an active agent via balloon dilatation offers an ideal possibility of treatment as this treatment can be repeated several times if necessary, and from a therapeutic aspect is able to achieve the same or clearly better results than the new implantation of a stent.

Moreover, the catheter balloons coated or filled according to the invention are especially suitable for the treatment of small vessels, preferably small blood vessels. Vessels having a vessel diameter smaller than 2.5 mm, preferred smaller than 2.2 mm are referred to as small vessels.

EXAMPLES

Example 1

Figure 1:
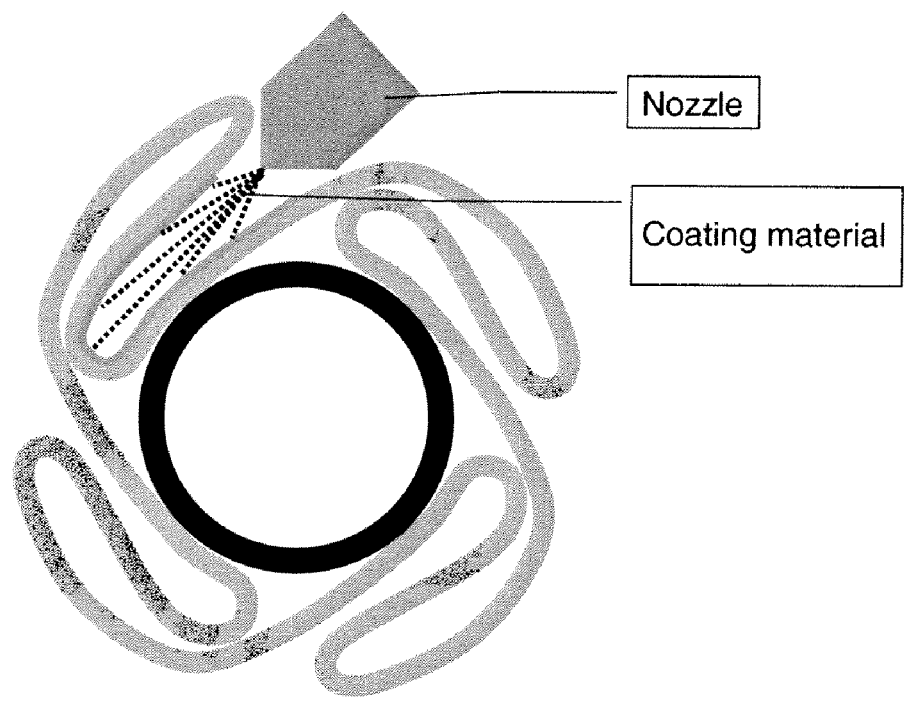
FIG. 1 shows a folded catheter balloon having four folds in the not dilated state, wherein a fold is being filled via a spraying nozzle with a composition of contrast agent, active agent and solvent.
Figure 2:
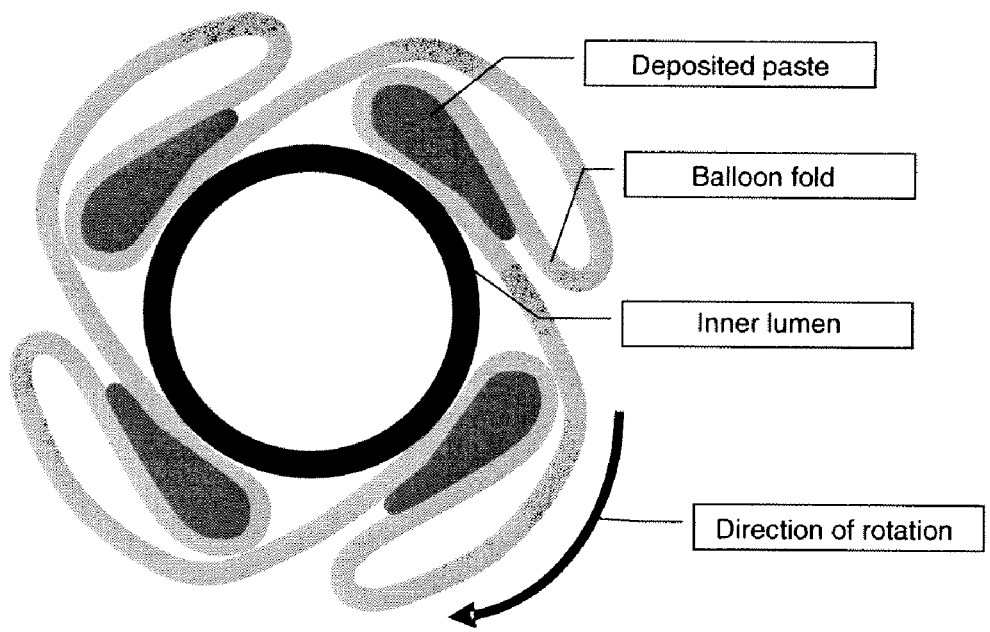
FIG. 2 shows a folded catheter balloon which is completely filled in all of the four folds in the not expanded state, wherein the composition within the folds is dried during the rotation of the folded catheter balloon resp. during the solvent is removed.

A common folded catheter balloon having four folds is filled in the folded state with a composition of iopromid, which is commercially available as a solution under the trade mark Ultravist®, paclitaxel, glycerine and ethanol by means of a spraying nozzle.

The composition contains 0.150 g of iopromid, 0.300 g of paclitaxel, 0.220 g of glycerine and 1.130 g of ethanol.

In each fold about 174 µg-621 µg of the composition is inserted.

After filling of all of the folds the folded catheter balloon is rotated for 1 minute in the direction of the fold openings and dried over night.

In total 696 µg-2484 µg of the dried composition were inserted portioned in four folds.

Example 2

About 10 mg of KMnO$_4$ are dissolved in 500 µl of water and as much PVP as possible is added. The mass is distributed on a polypropylene substrate and dried over night at room temperature.

From this brittle mass 4.5 mg are dissolved in 0.5 ml of chloroform or 0.6 ml of methanol or 0.8 ml of DMSO. Not dissolved particles can be filtered off. To this solution 100 µg of paclitaxel are added and after addition of 12.0 µg of linseed oil the resulting solution is sprayed by 4 nozzles being in series with a distance of 2 mm to each other equally into a fold via the fold spraying method described above.

After coating the first fold in the horizontal state the coating is dried without vacuum and the balloon comprising four folds is rotated about 90 degrees to coat the next fold which is above.

After coating all of the folds drying in vacuum is done under rotation of the catheter balloon according to the rotational drying method described above.

Example 3

Paclitaxel (250 mg) or rapamycin (250 mg) or a combination of paclitaxel (150 mg) and rapamycin (150 mg) is dissolved or suspended in an aqueous medium having an ethanol proportion of about 5% by volume and at a pH value from 4 to 5 and then mixed with a solution of phosphatidylserine and phosphatidylcholine in the weight ratio of 50:50.

A liposomal formulation is formed in which the active agent or the active agent combination is included in the vesicles.

The extraction of the liposomes from the aqueous solution is done by ultra filtration, wherein an extraction of the liposomes is not mandatory.

The extracted liposomes or the liposomal aqueous solution is filled into a cavity and filled into a fold via the pipetting method described above, wherein a capillary in an angle of about 40 degrees is set at the distal end of the fold. The catheter balloon is positioned horizontal and the fold to be coated lies above. Due to capillary forces the composition draws itself into the fold within about 48 seconds. Before the composition reaches the proximal end of the fold the capillary is removed such that also the composition which is present at the setting point of the capillary is drawn into the fold.

The coated catheter balloon is then dried at air and then finally dried by the rotational drying method described above.

Example 4

400 mg of trapidil are mixed with 1 ml of safflower oil and simultaneously inserted into the four folds of a folded catheter balloon via the syringe method described above.

The delivery openings of the delivery device are set at the distal end of the respective fold and moved in the fold with a rate of 1 cm per minute in the direction of the proximal end while a continuous flow of an oily trapidil solution is delivered into the fold.

Drying of the coated or filled folds is not necessary. Each fold was filled with about 1.5 mg of oily trapidil composition.

Example 5

300 mg of rapamycin are dissolved in 1 ml of acetic acid ester and mixed with 200 mg of EPA (5,8,11,14,17-eicosapentaenoic acid). By adding ethanol the viscosity can be adjusted such that a sprayable mixture results.

By the fold spraying method described above all of the 6 folds of a folded catheter balloon are simultaneously coated. The spraying device is comprised of an arrangement of in total 6 rows of respectively three spraying nozzles. The rows of respectively three spraying nozzles are supported on a rotational frame and can be inserted individually into the respective fold of the folded catheter balloon.

If the rows of spraying nozzles are properly placed the active agent-containing composition is delivered from each nozzle under the respective fold.

The catheter balloon is preferably in a perpendicular position and the three nozzles of a spraying row have a distance of 3 mm to each other.

After coating of the folds what can be done also in intervals the coated folds are dried at air under normal pressure and at room temperature and if necessary can be dried further at a temperature of 50° C. to 70° C. under normal pressure.

The folded catheter balloon was coated in the folds with totally 76 mg of solids.

Example 6

A solution of 250 µg of paclitaxel in a mixture of ethanol, n-butanol and ethyleneglycol in the volume ratio of 50:25:25 is prepared and to this solution 200 µg of vitamin A are added.

This composition is then filled into a delivery device having in total 4 cannules. Each of these four cannules is set at one of the four folds of a folded catheter balloon in a sharp angle of about 30 degrees and the four folds are simultaneously filled via the pipetting method described above.

After filling the catheter balloon is slowly rotated and simultaneously vacuum is applied and the rotational rate is increased with increasing vacuum for a short period of up to 1,200 rotations and the content of the fold is dried according to the rotational drying method described above.

Example 7

Borage oil or linseed oil and paclitaxel are mixed with each other in the weight ratio of 80 to 20 and dissolved in the mixing ratio of 1:1 in chloroform or DMSO such that a viscous composition is obtained.

This composition is filled via the syringe method described above in a fold of a folded catheter balloon having in total 5 folds. Therefore the catheter balloon is fixed and rotated such that the needle of the delivery device can be inserted into the fold to be filled. The needle is inserted at the proximal end of the catheter balloon into the fold up to about the middle and during a time of about 50 seconds the needle is moved continuously in the longitudinal direction of the fold while a continuous flow of viscous active agent-containing composition is delivered into the fold.

The average coating mass of the composition per fold can be between 0.4 and 2.8 mg depending on the design of the fold. In the present case the average coating mass of the composition per fold is about 0.8 mg in the dried state.

After filling all of the 5 folds the catheter balloon is dried under using the rotational drying method described above.

The folded catheter balloon was filled resp. coated with totally about 4.0 mg of dried composition.

Example 8

500 µg of paclitaxel is dissolved in 1 ml of anhydrous ethanol and 0.4 ml of acetic acid and filled into the folds of a catheter balloon via the pipetting method described above.

Subsequent drying is done after evaporation of the solvent according to the rotational drying method described above.

After coating and drying about 10 μg of paclitaxel are present in each fold.

Example 9

200 μg of paclitaxel are dissolved in 0.5 ml of ethanol and 0.5 ml of DMSO and 0.1 ml of acetic acid. Moreover, a solution of 350 μg of potassium acetate in ethanol—water is prepared in the volume ratio of 90:10. The potassium acetate solution is added to the paclitaxel solution and the solvents can evaporate until the first components start precipitating or the composition starts to get cloudy or a medium viscous composition is obtained.

This composition is inserted into the folds of the catheter balloon via the syringe method or the pipetting method described above. According to the invention the folds can be filled individually or in series or can also be filled simultaneously together. After evaporation of the solvent the final drying is done according to the rotational drying method as described above.

Example 10a

500 μg of rapamycin and 25 mg of iopamidol are dissolved in 1 ml of ethanol.

This solution can be inserted in the present form into the folds of the catheter balloon via the fold spraying method described above, wherein the folds can be coated individually or simultaneously as described above.

Drying is done preferably via the rotational drying method described above.

Example 10b

The solution from example 10a is adjusted to a viscosity of $10^3$ to $10^4$ mPa·s by adding propyleneglycol and/or glycerine.

The as-obtained composition is inserted into the folds according to the pipetting method described above, wherein the folds can be filled individually after each other or simultaneously together.

Final drying is done preferably via the rotational drying method described above.

Example 10c

The solution from example 10a or from example 10b is adjusted to a viscosity of above $10^4$ mPa·s by adding an oil selected from the group consisting of linseed oil, flax oil, hempseed oil, corn oil, walnut oil, rape oil, soy bean oil, sun flower oil, poppy-seed oil, safflower oil, wheat germ oil, safflower oil, grape-seed oil, evening primrose oil, borage oil, black cumin oil.

The as-obtained composition is inserted into the folds of the catheter balloon via the spraying method as described above, wherein the folds can be filled individually after each other or simultaneously together.

Final drying, if necessary, is done preferably via the rotational drying method described above.

The invention claimed is:

1. Method of coating or filling the folds of a folded catheter balloon comprising the following steps:
    a) providing a composition comprising at least a contrast agent and at least an antiproliferative, antiinflammatory, antiphlogistic, cytostatic, cytotoxic, antiangiogenic, anti-restenotic or antithrombotic active agent and at least an alcohol as solvent;
    b) inserting the composition comprising at least a contrast agent and at least an antiproliferative, antiinflammatory, antiphlogistic, cytostatic, cytotoxic, antiangiogenic, anti-restenotic or antithrombotic active agent and at least an alcohol as solvent selectively into the folds of the folded catheter balloon by means of a syringe device, wherein only the folds of the folded catheter balloon are coated or filled selectively and the surface of the folded catheter balloon outside the folds is not coated;
    c) drying the composition comprising at least a contrast agent and at least an antiproliferative, antiinflammatory, antiphlogistic, cytostatic, cytotoxic, antiangiogenic, anti-restenotic or antithrombotic active agent and at least an alcohol as solvent by removing the solvent via evaporation or under reduced pressure.

2. Method according to claim 1, wherein a syringe nozzle is used as syringe device which is inserted into the folds of the folded catheter balloon and the folds are filled under pressure with the composition comprising at least a contrast agent and at least an antiproliferative, antiinflammatory, antiphlogistic, cytostatic, cytotoxic, antiangiogenic, anti-restenotic or antithrombotic active agent and at least an alcohol as solvent.

3. Method according to claim 1, wherein the folded catheter balloon is coated or filled in the compressed or deflated state or at maximum 10% inflated state.

4. Method according to claim 1, wherein two or more or all of the folds of the folded catheter balloon are filled or coated simultaneously.

5. Method according to claim 1, wherein after the filling or coating of one or more folds of the folded catheter balloon it is rotated in the direction of the fold openings.

6. Method according to claim 1, wherein the composition contains at least an alcohol as solvent selected from the group comprising:
    methanol, ethanol, isopropanol, n-butanol, iso-butanol, t-butanol, ethyleneglycol, propyleneglycol, 1,3-propanediol, butyleneglycol, 1,3-butanediol, 1,4-butanediol, glycerin, 1,2,3-butanetriol, 1,2,4-butanetriol and 1,2,3,4-butanetetraol.

7. Method according to claim 1, wherein the composition contains at least a contrast agent selected from the group comprising:
    x-ray contrast agents, iodine-containing contrast agents, contrast agents having a 1,3,5-triiodobenzene nucleus, nephrotropic x-ray contrast agents having low osmolarity, amidotrizoic acid, iothalaminic acid, iotrolan, iopamidol, iodoxaminic acid, diatrizoic acid, iomeprol, iopromid, desmethoxyacetyl-iopromid (DAMI), 5-amino-2,4,6-triiodophthalic acid-(2,3-dihydroxypropyl)-amide (ATH).

8. Method according to claim 1, wherein the composition contains at least an oil and/or at least a fatty acid selected from the group comprising:
    linseed oil, flax oil, hempseed oil, corn oil, walnut oil, rape oil, soy bean oil, sun flower oil, poppy-seed oil, safflower oil, wheat germ oil, safflower oil, grape-seed oil, evening primrose oil, borage oil, black cumin oil, algae oil, fish oil, cod-liver oil, taririnic acid, ximeninic acid, stearolinic acid, 6,9-octadeceninic acid, pyrulinic acid, crepenynic acid, heisterinic acid, ETYA, linoleic acid, γ-linolenic acid, dihomo-γ-linolenic acid, arachidonic acid, α-linolenic acid, stearidonic acid, EPA, DPA, DHA, meadic acid, stellaheptaenic acid, taxolic acid, pinolenic acid, sciadonic acid, myristoleic acid, palmitoleic acid, petroselinic acid, oleic acid, vaccenic acid, gadoleinic acid, gondoinic acid, erucinic acid, nervonic acid, elaidinic acid, t-vaccenic acid, laurinic acid, myristinic acid, palmitinic acid, margarinic acid, stearinic acid, arachinic acid, behenic acid, lignocerinic acid, 6,8-dithianoctanoic acid, γ-linolenic acid, α-liponic acid.

9. Method according to claim 1, wherein the at least one antiproliferative, antiinflammatory, antiphlogistic, cytostatic, cytotoxic, antiangiogenic, anti-restenotic or antithrombotic active agent is selected from the group comprising: abciximab, acemetacin, acetylvismione B, aclarubicin, ademetionine, adriamycin, aescin, afromoson, akagerine, aldesleukin, amidorone, aminoglutethemide, amsacrine, anakinra, anastrozole, anemonin, anopterine, antimycotics, antithrombotics, apocymarin, argatroban, aristolactam-AII, aristolochic acid, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, Boswellic acids and derivatives thereof, bruceanoles A, B and C, bryophyllin A, busulfan, antithrombin, bivalirudin, cadherins, camptothecin, capecitabine, o-carbamoyl-phenoxy-acetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-type Natriuretic Peptide (CNP), cudraisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, daunomycin, epirubicin, epothilones A and B, erythromycin, estramustine, etoposide, everolimus, filgrastim, fluoroblastin, fluvastatin, fludarabine, fludarabine-5'-dihydrogenphosphate, fluorouracil, folimycin, fosfestrol, gemcitabine, ghalakinoside, ginkgol, ginkgolic acid, glycoside 1a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, irinotecan, topotecan, hydroxycarbamide, miltefosine, pentostatin, pegaspargase, exemestane, letrozole, formestane, SMC proliferation inhibitor-2ω, mitoxantrone, mycophenolate mofetil, c-myc antisense, b-myc antisense, β-lapachone, podophyllotoxin, podophyllic acid 2-ethylhydrazide, molgramostim (rhuGM-CSF), peginterferon α-2b, lanograstim (r-HuG-CSF), macrogol, selectin (cytokine antagonist), cytokinin inhibitors, COX-2 inhibitor, NFkB, angiopeptin, monoclonal antibodies which inhibit the muscle cell proliferation, bFGF antagonists, probucol, prostaglandins, 1-hydroxy-11-methoxycanthin-6-one, scopoletin, NO donors, pentaerythritol tetranitrate, sydnonimines, S-nitrosoderivatives, tamoxifen, staurosporine, β-estradiol, α-estradiol, estriol, estrone, ethinylestradiol, medroxyprogesterone, estradiol cypionates, estradiol benzoates, tranilast, kamebakaurin and other terpenoids which are applied in the therapy of cancer, verapamil, tyrosine kinase inhibitors (tyrphostins), paclitaxel, derivatives and analoga of paclitaxel, 6-α-hydroxy-paclitaxel, 2'-succinylpaclitaxel, 2'-succinylpaclitaxeltriethanolamine, 2'-glutarylpaclitaxel, 2'-glutarylpaclitaxeltriethanolamine, 2'-O-ester of paclitaxel with N-(dimethylaminoethyl)glutamide, 2'-O-ester of paclitaxel with N-(dimethylaminoethyl) glutamidhydrochloride, taxotere, macrocyclic oligomers of carbon suboxide (MCS), mofebutazone, lonazolac, lidocaine, ketoprofen, mefenamic acid, piroxicam, meloxicam, penicillamine, hydroxychloroquine, sodium aurothiomalate, oxaceprol, β-sitosterin, myrtecaine, polidocanol, nonivamide, levomenthol, ellipticine, D-24851 (Calbiochem), colcemid, cytochalasin A-E, indanocine, nocadazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics, cefadroxil, cefazolin, cefaclor, cefoxitin, tobramycin, gentamycin, penicillins, dicloxacillin, oxacillin, sulfonamides, metronidazole, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamine, prourokinase, streptokinase, warfarin, urokinase, vasodilators, dipyridamol, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, p65, NF-kB, Bcl-xL antisense oligonucleotides, halofuginone, nifedipine, tocopherol, tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecainide, propafenone, sotolol, natural and synthetically obtained steroids, inotodiol, maquiroside A, ghalakinoside, mansonine, strebloside, hydrocortisone, betamethasone, dexamethasone, non-steroidal substances (NSAIDS), fenoprofen, ibuprofen, indomethacin, naproxen, phenylbutazone, antiviral agents, ayclovir, ganciclovir, zidovudin, clotrimazole, flucytosine, griseofulvin, ketoconazole, miconazole, nystatin, terbinafine, antiprotozoal agents, chloroquine, mefloquine, quinine, natural terpenoids, hippocaesculin, barringtogenol-C21-angelat, 14-dehydroagrostistachin, agroskerin, agrostistachin, 17-hydroxyagrostistachin, ovatodiolids, 4,7-oxycycloanisomel acid, baccharinoids B1, B2, B3 and B7, tubeimoside, bruceantinoside C, yadanziosides N and P, isodeoxyelephantopin, tomenphantopin A and B, coronarin A, B, C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterin, protoanemonin, cheliburin chloride, sinococuline A and B, dihydronitidine, nitidine chloride, 12-beta-hydroxypregnadien-3,20-dion, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, maytansin, lycoridicin, margetine, pancratistatin, liriodenine, bisparthenolidine, oxoushinsunine, periplocoside A, ursolic acid, deoxypsorospermin, psycorubin, ricin A, sanguinarine, manwu wheat acid, methylsorbifolin, spatheliachromen, stizophyllin, mansonine, strebloside, dihydrousambaraensine, hydroxyusambarine, strychnopentamine, strychnophylline, usambarine, usambarensine, liriodenine, oxoushinsunine, daphnoretin, lariciresinol, methoxylariciresinol, syringaresinol, sirolimus, rapamycin, somatostatin, tacrolimus, roxithromycin, troleandomycin, simvastatin, rosuvastatin, vinblastine, vincristine, vindesine, teniposide, vinorelbine, trofosfamide, treosulfan, temozolomide, thiotepa, tretinoin, spiramycin, umbelliferone, desacetylvismione A, vismione A and B, zeorin.

10. Method according to claim 9, wherein the at least one antiproliferative, antiinflammatory, antiphlogistic, cytostatic, cytotoxic, antiangiogenic, anti-restenotic or antithrombotic active agent is selected from the group comprising:

paclitaxel, derivatives and analogues of paclitaxel, 6-α-hydroxy-paclitaxel, 2'-succinylpaclitaxel, 2'-succinylpaclitaxeltriethanol-amine, 2'-glutarylpaclitaxel, 2'-glutarylpaclitaxeltriethanolamine, 2'-O-ester of paclitaxel with N-(dimethylaminoethyl)glutamide, 2'-O-ester of paclitaxel with N-(dimethylaminoethyl)glutamidehydrochloride, taxotere.

* * * * *